US00PP31193P2

(12) United States Plant Patent
Zaiger et al.

(10) Patent No.: US PP31,193 P2
(45) Date of Patent: Dec. 10, 2019

(54) PEACH TREE NAMED 'SUMMER GLORY'

(50) Latin Name: *Prunus persica*
Varietal Denomination: Summer Glory

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 16/350,678

(22) Filed: Dec. 19, 2018

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./197
See application file for complete search history.

*Primary Examiner* — Susan McCormick Ewoldt

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Clingstone fruit with firm, yellow flesh.
4. Fruit with very good flavor and eating quality.
5. Fruit having an attractive dark red skin color.

1 Drawing Sheet

Botanical designation: *Prunus persica.*
Variety denomination: 'Summer Glory'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Sierra Rich' Peach (U.S. Plant Pat. No. 12,391), 'Sweet Henry' Peach (U.S. Plant Pat. No. 16,068) and the proprietary non-patented peach seedling selections '358LN360', '79EG632' and '66EG140'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. from a first generation cross between our proprietary non-patented peach seedling selection '358LN360' and 'Sweet Henry' Peach (U.S. Plant Pat. No. 16,068). The proprietary non-patented peach seed parent '358LN360' originated from a cross between our proprietary non-patented peach seedling selections '79EG632' and '66EG140'. We planted and maintained a large group of these first generation seedlings on their own root system, during which time one seedling, which is the present variety, exhibited desirable tree and fruit characteristics and was selected in 2013 for asexual propagation and commercialization.

ASEXUAL REPRODUCTION OF THE VARIETY

In 2013 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a regular and productive bearer of large size, yellow flesh, clingstone fruit. The fruit is further characterized by its firm flesh, very good flavor and eating quality with good storage and shipping ability. In comparison to its seed parent (358LN360) the fruit of the new variety is approximately 21 days earlier in maturity. In comparison to its pollen parent 'Sweet Henry' Peach (U.S. Plant Pat. No. 16,068) the fruit of the new variety is approximately 40 days earlier in maturity. In comparison to the commercial variety 'Sierra Rich' Peach (U.S. Plant Pat. No. 12,391) the fruit of the new variety is larger in size and is approximately 8 days later in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color published in 1958.

Tree:

*Size.*—Large, usually pruned to 3 to 3.5 meters in height and width for economical harvesting of fruit. Size varies with different cultural practices.

*Vigor.*—Vigorous, growth of 1.5 to 2 meters in height the first growing season. Varies slightly with type and fertility of soil, climatic conditions and cultural practices.

*Form.*—Upright, usually pruned to vase shape.

*Branching Habit.*—Upright, crotch angle approximately 25°, increases with heavy crop load.

*Productivity.*—Productive, thinning and spacing of fruit necessary for desired market size fruit. Number of fruit set varies with climatic conditions during blooming period.

*Bearer.*—Regular, has had adequate fruit set 4 consecutive years. No alternate bearing observed.

*Fertility.*—Self fertile.

*Density.*—Medium dense, usually pruned to vase shape to increase air movement and sunlight to enhance fruit color and health of fruit wood.

*Hardiness.*—Hardy in all stone fruit growing areas of California. Tree grown in USDA Hardiness Zone 9. Winter chilling requirement approximately 650 hours at or below 45° F.

Trunk:

*Size.*—Large, average circumference 68.6 cm at 22.9 cm above ground on a 5 year old tree.

*Stocky.*—Medium stocky.

*Texture.*—Medium shaggy, roughness increases with age.

*Color.*—10YR 2/2.

Branches:

*Size.*—Medium. Average circumference 12.2 cm at 1.2 meters above ground. Crotch angle approximately 25°, increases with heavy crop load.

*Surface Texture.*—New growth relatively smooth. Mature growth medium rough, roughness increases with age.

*Lenticels.*—Average number 28 in a 25.8 square cm area. Average length 2.8 mm. Average width 1.8 mm. Color 10YR 4/8 to 10YR 5/6.

*Color.*—New growth 2.5GY 7/6. Mature growth varies from 7.5YR 4/2 to 7.5YR 3/2, varies with age of growth.

Leaves:

*Size.*—Large. Average length 164.7 mm. Average width 44.7 mm.

*Form.*—Lanceolate.

*Apex.*—Acuminate.

*Base.*—Cuneate.

*Margin.*—Serrate.

*Thickness.*—Medium.

*Surface Texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Average length 14.7 mm. Average width 1.9 mm. Longitudinally grooved. Surface — glabrous. Color varies from 2.5GY 5/6 to 5GY 5/4.

*Glands.*—Type — reniform. Size — small. Average length 0.7 mm. Average diameter 0.5 mm. Number varies from 2 to 5, average number 3. Located primarily on upper portion of the petiole and base of leaf blade. Color 2.5GY 5/8.

*Stipules.*—None present at time of measurement.

*Color.*—Upper surface varies from 5GY 3/6 to 7.5GY 3/4. Lower surface varies from 5GY 4/4 to 7.5GY 4/4. Midvein color varies from 2.5GY 8/4 to 2.5GY 7/4.

Flower buds:

*Size.*—Large. Average length 22.5 mm. Average diameter 11.3 mm.

*Hardiness.*—Hardy with respect to California winters.

*Density.*—Medium dense.

*Form.*—Elongated.

*Pedicel.*—Average length 3.6 mm. Average width 1.1 mm. Surface — glabrous. Color varies from 2.5GY 5/8 to 5GY 6/6.

*Color.*—Varies from 7.5RP 6/12 to 7.5RP 8/4.

Flowers:

*Blooming Period.*—Date of First Bloom Feb. 16, 2018. Date of Petal Fall Feb. 26, 2018, varies slightly with climatic conditions.

*Size.*—Large. Average height 24.0 mm. Average diameter 50.4 mm.

*Petals.*—Normally 5, alternately arranged to sepals. Size — large. Average length 24.4 mm. Average width 21.1 mm. Petal apex rounded. Petal base truncate. Form — obovate. Arrangement — overlapping. Margin — sinuate. Color varies from 5RP 7/8 to 5RP 8/4, fades with age of flower.

*Sepals.*—Normally 5, alternately arranged to petals. Size — large. Average length 8.0 mm. Average width 7.1 mm. Sepal apex — rounded to triangular. Shape — triangular. Margin — entire. Color— upper surface varies from 5GY 5/8 to 5R 3/4. Lower surface varies from 5R 3/4 to 5R 2/4. Surface — upper surface glabrous, lower surface pubescent.

*Stamens.*—Average number per flower 44. Average filament length 17.2 mm. On average, the stamens are above the height of the petals. Filament color varies from N 9.5/ (white) to 5RP 7/6. Anther color varies from 7.5R 3/10 to 5Y 8/8.

*Pollen.*—Self fertile. Color varies from 2.5Y 8/14 to 2.5Y 7/10.

*Pistil.*—Number — normally one. Average length 21.9 mm. Surface — pubescent. Position of stigma even with anthers. Color varies from 10Y 8.5/6 to 10Y 8/6.

*Fragrance.*—Wanting.

*Color.*—Varies from 5RP 8/4 to 7.5RP 8/6.

*Pedicel.*—Average length 4.9 mm. Average width 1.3 mm. Surface — glabrous. Color varies from 2.5GY 6/8 to 5GY 5/8.

*Number Flowers per Flower Bud.*—Normally one.

Fruit:

*Maturity When Described.*—Firm ripe and ready for consumption.

*Date of First Picking.*—Jul. 2, 2018.

*Date of Last Picking.*—Jul. 12, 2018, varies slightly with climatic conditions.

*Size.*—Large. Average diameter axially 75.5 mm. Average transversely in suture plane 80.5 mm. Average weight 286.0 grams, varies slightly with fertility of the soil, amount of thinning and climatic conditions.

*Form.*—Globose.

*Suture.*—Slightly lipped.

*Ventral Surface.*—Slightly lipped.

*Apex.*—Slightly retuse.

*Base.*—Retuse.

*Stem Cavity.*—Rounded to slightly elongated in suture plane. Average depth 13.5 mm. Average diameter 9.3 mm.

Stem:

*Size.*—Small. Average length 7.2 mm. Average diameter 3.2 mm.

*Color.*—Varies from 5GY 6/8 to 2.5GY 6/8.

Flesh:

*Ripens.*—Evenly.

*Texture.*—Firm, meaty.

*Fibers.*—Few, small, tender.

*Firmness.*—Good, comparable to other commercial peach varieties.

*Aroma.*—Moderate.

*Amydgalin.*—Undetected.

*Eating Quality.*—Very good.

*Flavor.*—Very good, with a good balance between acid and sugar.

*Juice.*—Moderate amount, enhances flavor.

*Acidity.*—Not available.

*Brix.*—Average Brix 13.0°, varies slightly with amount of fruit per tree and climatic conditions.

*Color.*—Varies from 5Y 8/8 to 5R 4/8 where anthrocyanin color is present.

*Pit Cavity.*—Average length 40.7 mm. Average width 28.7 mm. Average depth 12.5 mm. Color varies from 2.5Y 8/8 to 7.5R 3/8.

Skin:

*Thickness.*—Medium.

*Surface.*—Smooth.

*Pubescence.*—Moderate amount, short in length.

*Tendency to Crack.*—None.

*Color.*—Ground color varies from 2.5Y 7/8 to 2.5Y 8/6. Overspread with 5R 3/4 to 5R 4/10.

*Tenacity.*—Tenacious to the flesh.

*Astringency.*—Slight to none.

Stone:

*Type.*—Clingstone, medium adherence to flesh.

*Size.*—Large. Average length 39.7 mm. Average width 27.7 min. Average thickness 23.0 mm.

*Form.*—Obovoid.

*Base.*—Flat.

*Apex.*—Pointed. Average length 3.0 mm.

*Surface.*—Pitted throughout, pits vary from rounded to elongated.

*Sides.*—Unequal, one side extending further outward from suture plane.

*Ridges.*—Small, narrow ridges extending from base toward apex.

*Tendency to Split.*—None.

*Color.*—Varies from 5R 3/8 to 7.5R 2/8 when dry.

Kernel:

*Size.*—Large. Average length 20.2 mm. Average width 11.4 mm. Average depth 6.4 mm.

*Form.*—Ovate.

*Viability.*—Viable, complete embryo development.

*Skin Color.*—Varies from 2.5Y 8.5/8 to 2.5Y 8/10.

Use:

*Dessert.*—Market — local and long distance.

KEEPING QUALITY

Good, held firm in cold storage 3 weeks at 38° to 42° F. without shriveling, internal breakdown of flesh or appreciable loss of flavor.

SHIPPING QUALITY

Good, showed minimal skin scarring or flesh bruising during picking, packing and shipping trials.

PLANT/FRUIT DISEASE RESISTANCE/SUSCEPTIBILITY

No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

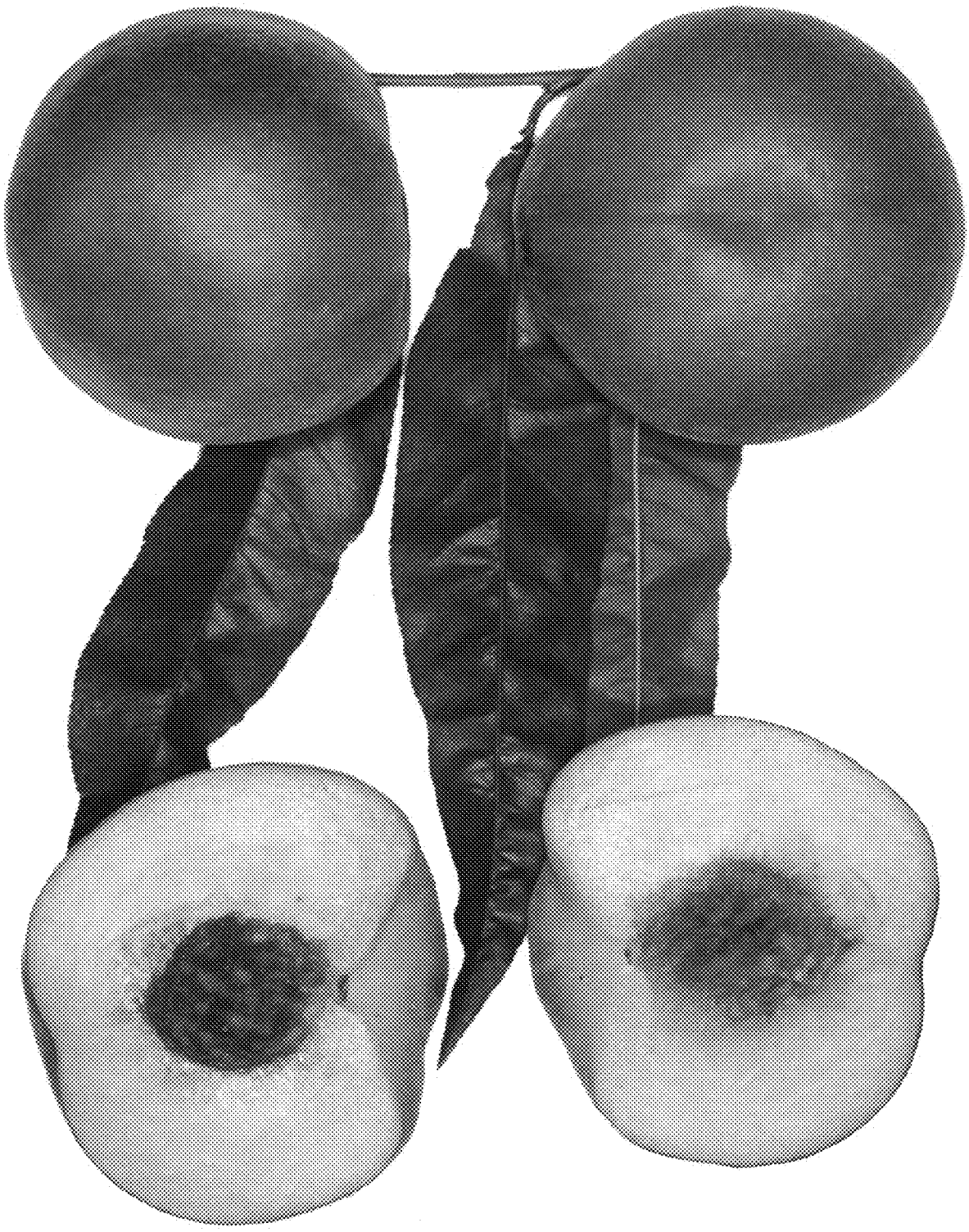

* * * * *